US007175845B2

(12) United States Patent
Dertzbaugh

(10) Patent No.: US 7,175,845 B2
(45) Date of Patent: Feb. 13, 2007

(54) MONOCLONAL ANTIBODIES AGAINST RICIN TOXIN AND METHODS OF MAKING AND USING THEREOF

(75) Inventor: Mark T. Dertzbaugh, Fairfield, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 77 days.

(21) Appl. No.: 10/896,875

(22) Filed: Jul. 23, 2004

(65) Prior Publication Data

US 2007/0009510 A1 Jan. 11, 2007

Related U.S. Application Data

(60) Provisional application No. 60/490,295, filed on Jul. 25, 2003.

(51) Int. Cl.
*A61K 39/395* (2006.01)

(52) U.S. Cl. .............................. 424/141.1; 530/387.1; 435/325

(58) Field of Classification Search .............. 424/133.1
See application file for complete search history.

(56) References Cited

U.S. PATENT DOCUMENTS 5,626,844 A 5/1997 Lemley
5,858,682 A 1/1999 Gruenwald

OTHER PUBLICATIONS

Casadevall, Emerging Infectious Diseases, vol. 8, No. 8, pp. 833-841, 2002.*
Colombatti et al. (1987) "Identification and Characterization of a Monoclonal Antibody Recognizing a Galactose-Binding Domain of the Toxin Ricin" J. Immunol. 138(9):3339-3344.
Colombatti et al. (1986) "Monoclona Antibodies Against Ricin: Effects on Toxin Function" Hybridoma 5(1):9-19.
Lemley et al. (1994) "Identification and Characterization of a Monoclonal Antibody that Neutralizes Ricin Toxicity in Vitro and in Vivo" Hybridoma 13(5):417-421.
Poli et al. (1996) "Aerosolized Specific Antibody Protects Mice from Lung Injury Associated with Aerosolized Ricin Exposure" Toxicon 34(9):1037-1044.
Shyu et al. (2002) "Monoclonal Antibody-Based Enzyme Immunoassay for Detection of Ricin" Hybridoma and Hybridomics 21(1):69-73.

* cited by examiner

*Primary Examiner*—Christina Chan
*Assistant Examiner*—Yunsoo Kim
(74) *Attorney, Agent, or Firm*—Elizabeth Arwine

(57) ABSTRACT

Disclosed herein are monoclonal antibodies (Mabs) against ricin toxin and its subunits. The Mabs were initially selected based upon their ability to bind to ricin and its individual subunits in a solid-phase enzyme-linked immunoassay (ELISA). Several candidates were selected for further evaluation, including their ability to inhibit ricin intoxication in vitro and for their utility as immunodiagnostic reagents. As disclosed herein, the Mabs may be used in immunoassays. Also disclosed, are use of the Mabs to inhibit ricin-mediated eukaryotic cell cytotoxicity in vitro, thereby indicating that these Mabs may be used to prevent and treat ricin intoxication in vivo. Kits comprising the Mabs are also disclosed.

7 Claims, 1 Drawing Sheet

MONOCLONAL ANTIBODIES AGAINST RICIN TOXIN AND METHODS OF MAKING AND USING THEREOF

CROSS REFERENCE TO RELATED APPLICATIONS

This application claims the benefit of U.S. Provisional Patent Application No. 60/490,295, filed 25 Jul. 2003, which names Mark T. Dertzbaugh as the inventor and is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to ricin toxin. In particular, the present invention relates to ricin vaccines, compositions and therapeutics as well as methods of making and using thereof.

2. Description of the Related Art

Ricin is a very toxic protein obtained from the castor bean, *Ricinus communis, Euphorbiaceae*. Ricin is a heterodimer comprising an A chain and a B chain joined by a disulfide bond. Ricin A chain (RTA) is an N-glycosidase enzyme that irreversibly damages a specific adenine base from 28S rRNA. Once the rRNA has been damaged, the cell cannot make protein and will inevitably die (cytotoxicity). As RTA exhibits this type of destructive catalytic activity, RTA is commonly referred to as a type II ribosome inactivating protein (RIP). See Lord, et al. (1991) Semin. Cell Biol. 2(1):15–22. RTA has been coupled with a targeting moiety to selectively destroy target cells such as tumor cells. See U.S. Pat. Nos. 4,980,457; 4,962,188; and 4,689,401; see also Vitetta et al. (1993) Trends Pharmacol. Sci. 14:148–154 and Ghetie & Vitetta (1994) Cancer Drug Delivery 2:191–198.

The toxic consequences of ricin are due to the biological activity of RTA. Ricin B chain (RTB) binds the toxin to cell surface receptors and then RTA is transferred inside the cell where inhibition of ribosome activity occurs. The human lethal dose of ricin toxin is about 1 µg/kg. As highly purified ricin is readily available using methods known in the art, the use of ricin toxin in biological warfare and terrorism is highly possible and probable.

Ricin toxin (RT) or *Ricin communis* agglutinin II (RCA 60), a glycoprotein produced by the castor bean plant, *Ricin communis*, is composed of two subunits, about a 30 kDa enzymatically active A subunit (RTA) and about a 32 kDa B subunit (RTB). See Lord & Roberts (1994) Faseb J. 8(2): 201–208. The B-chain mediates receptor binding of the toxin to eukaryotic cells via its high affinity for galactose. See Alami & Taupiac (1997) Cell Biol. Int. 21(3): 145–150. Once internalized within the cell, the A chain causes catalytic depurination of the 28S ribosomal RNA that results in inhibition of protein synthesis. See Chen & Link (1998) Biochemistry 37(33):11605–11613. Ricin is highly toxic and can cause death when given in sufficient quantities by either systemic or inhalational routes of exposure. See Wilhelmsen & Pitt (1996) Vet. Pathol. 33(3):296–302.

Ricin is a Category B Agent on the Centers for Disease Control (CDC) Select Agent List and thus there is a strong interest in developing diagnostic tests for toxin identification in clinical and environmental samples. See Thomas, M. (2002) "Possession, use, and transfer of select agents and toxins; interim final rule." Federal Register 240(67). In addition, because there is no vaccine for ricin and no therapeutic agents available for treatment, there is a serious need to develop prophylactic and therapeutic countermeasures for ricin intoxication.

Development of antibodies recognizing determinants on the ricin molecule may be able to address several of these needs. Not only can antibodies be used for diagnostic reagents, but they can also neutralize the toxin by either preventing binding to cells or inhibiting enzymatic activity. There is evidence to suggest that antibodies can protect against ricin intoxication as animals were protected from lethality by administration of polyclonal antibody prior to exposure to ricin. See Hewetson & Rivera (1993) Vaccine 11(7):743–746; and Houston (1982) J. Clin. Toxicol. 19(4): 385–9. Anti-ricin IgG has also been shown to protect against inhalational challenge in animals, demonstrating the feasibility of using antibody to protect against this route of exposure as well. See Griffiths & Lindsay (1995) Hum. Exp. Toxicol. 14(2):155–164; and Poli & Rivera (1996) Toxicon. 34(9):1037–1044.

Although polyclonal antibody can be used for these purposes, monoclonal antibodies offer several potential advantages, including consistency and reproducibility of product and the ability to humanize the antibody molecule to reduce adverse reactions caused such as serum sickness when animal antibodies are used therapeutically. Several monoclonal antibodies (Mab) previously developed have been shown to confer protection against ricin intoxication in vitro. See Colombatti & Johnson (1987) J. Immunol. 138 (10):3339–33344; Colombatti & Pezzini (1986) Hybridoma 5(1):9–19; and Columbatti (1997) Personal communication to M. Dertzbaugh. However these Mabs were lost several years ago and to date only one Mab that still exists which has been shown to protect against ricin intoxication in vivo and this Mab is directed towards the A chain of the holotoxin. See Lemley & Amanatides (1994) Hybridoma 13(5):417–421.

Thus, a need exists for Mabs against ricin toxin.

SUMMARY OF THE INVENTION

The present invention provides monoclonal antibodies against ricin toxin and compositions and methods of using thereof.

In some embodiments, the present invention provides a monoclonal antibody having the binding characteristics to ricin toxin, ricin toxin A-chain, ricin toxin B-chain, or a combination thereof and an antibody produced by a hybridoma deposited in the American Type Culture Collection selected from the group consisting of ATCC accession numbers PTA-6105, PTA-6106, PTA-6107, PTA-6108, PTA-6109, and PTA-6110.

In some embodiments, the present invention provides a hybridoma deposited in the American Type Culture Collection selected from the group consisting of ATCC accession numbers PTA-6105, PTA-6106, PTA-6107, PTA-6108, PTA-6109, and PTA-6110.

In some embodiments, the present invention provides a monoclonal antibody produced by the hybridomas of the present invention.

In some embodiments, the present invention provides a composition comprising at least one monoclonal antibody of the present invention and a pharmaceutically acceptable carrier. The compositions may further comprise a supplementary active compound as described herein.

In some embodiments, the present invention provides a method of providing passive immunity against ricin intoxication in a subject comprising administering to the subject a therapeutically effective amount of at least one monoclonal antibody of the present invention. In some embodiments, the monoclonal antibody is produced by a hybridoma deposited in the American Type Culture Collection selected from the group consisting of ATCC accession numbers PTA-6106, PTA-6107, and PTA-6110.

In some embodiments, the present invention provides a method of treating, preventing, inhibiting, or modulating ricin intoxication in a subject comprising administering to the subject a therapeutically effective amount of at least one monoclonal antibody of the present invention. In some embodiments, the monoclonal antibody is produced by a hybridoma deposited in the American Type Culture Collection selected from the group consisting of ATCC accession numbers PTA-6106, PTA-6107, and PTA-6110.

In some embodiments, the present invention provides a method for assaying, detecting, measuring, or monitoring ricin toxin, ricin toxin A-chain, ricin toxin B-chain, or a combination thereof in a sample which comprises using at least one monoclonal antibody of the present invention as a detection reagent. In some embodiments, the monoclonal antibody is produced by a hybridoma deposited in the American Type Culture Collection selected from the group consisting of ATCC accession numbers PTA-6105, PTA-6108, and PTA-6109.

In some embodiments, the present invention provides a method for obtaining ricin toxin, ricin toxin A-chain, ricin toxin B-chain, or a combination thereof from a sample which comprises using at least one monoclonal antibody of the present invention as a capture reagent. In some embodiments, the monoclonal antibody is produced by a hybridoma deposited in the American Type Culture Collection selected from the group consisting of ATCC accession numbers PTA-6105, PTA-6108, and PTA-6109.

In some embodiments, the present invention provides a kit comprising at least one monoclonal antibody of the present invention packaged together with instructions for use. The kits may comprise other reagents including buffers, containers, controls, devices, and labels used in biological assays. The kits may comprise devices for administering the monoclonal antibodies to a subject.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
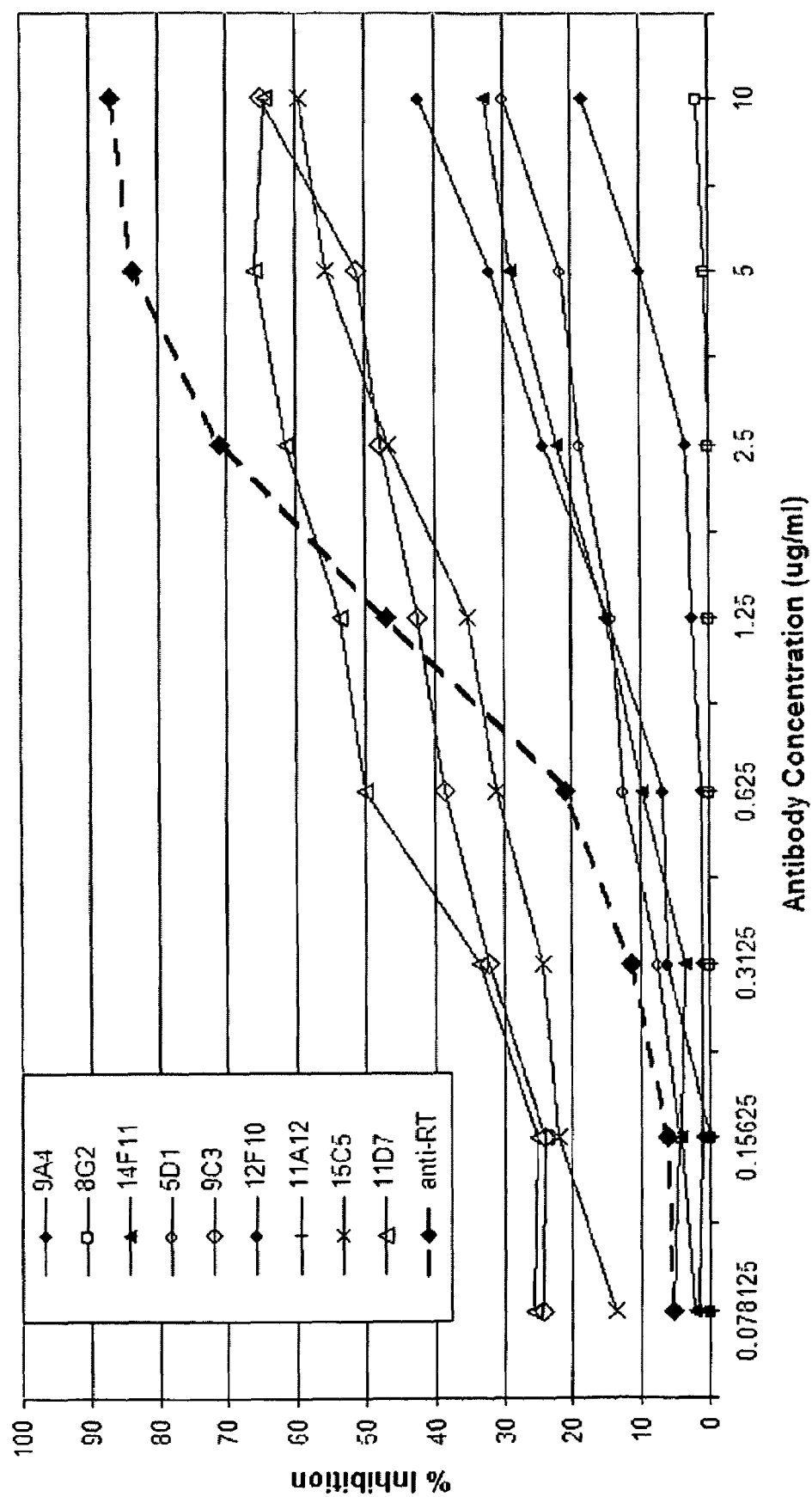
FIG. 1 shows the percent inhibition of ricin-mediated cellular cytotoxicity. Affinity purified Mab was serially diluted two-fold and mixed with ricin toxin prior to incubation with EL-4 cells. Cytotoxicity was determined using Alamar Blue as a vital stain. The $A_{570}$ was determined for each well and used to calculate percent inhibition relative to an untreated control. Affinity-purified polyclonal goat anti-mouse RT was used as a positive control.

Provided herein are monoclonal antibodies (Mabs) having activity against ricin toxin. The Mabs of the present invention may be used as immunodiagnostic reagents and for inhibiting ricin-induced cellular cytotoxicity. The Mabs of the present invention may be used in methods for treating, preventing, or inhibiting ricin intoxication.

As provided herein, mice were immunized with ricin A chain, ricin B chain, or holotoxin and their spleen cells were then isolated and immortalized by fusing them to myeloma cells. The resulting hybridomas were screened by ELISA using methods known in the art for their ability to produce Mabs that could bind to ricin toxin. Mabs that appeared to have high affinity for ricin were evaluated further for their use as diagnostic reagents and their ability to neutralize toxin in vitro.

Since the toxicity of ricin can be neutralized using polyclonal antibody, monoclonal antibodies or mixtures of monoclonal antibodies against ricin may be used to treat, prevent or inhibit ricin intoxication. See Colombatti et al. (1986) Hybridoma 5(1):9–19; Hewetson et al. (1993) Vaccine 11(7):743–746; Houston (1982) J. Toxicol. Clin. Toxicol. 19(4):385–389; Griffiths et al. (1995) Hum. Exp. Toxicol. 14(2):155–164; and Poli et al. (1996) Toxicon. 34(9): 1037–1044, which are herein incorporated by reference.

Several (MAb) have been raised that confer protection against ricin intoxication in vitro. Neutralizing MAbs have been raised to both the A chain (RTA) and the B chain (RTB) of ricin and have been previously published. See Colombatti et al. (1987) J. Immunol. 138(10):3339–3344, and Colombatti et al. (1986) Hybridoma 5(1):9–19, which are herein incorporated by reference. Unfortunately, most of these Mabs were lost in a freezer accident several years ago. Columbatti, personal communication. To date, only one Mab specific for RTA has been shown to protect against ricin intoxication in vivo. See U.S. Pat. No. 5,626,844, which is herein incorporated by reference.

The present invention provides additional ricin-specific neutralizing Mabs. The Mabs of the present invention may be used as a diagnostic reagent for detecting, measuring, or monitoring ricin or its subunits in a sample. The Mabs of the present invention may be administered to a subject prior, during, after, or a combination thereof to exposure or potential exposure to ricin intoxication, to include their use in for inhalational exposures. The Mabs of the present invention may be administered to a subject after exposure to ricin to treat ricin intoxication. The Mabs of the present invention may be used for affinity purification of ricin or its subunits. The Mabs of the present invention may be used as an antidote to treat ricin immunotoxin-conjugate induced toxicity from ricin chemotherapies. The Mabs may be used to identify epitopes of ricin that can confer protection in the form of a vaccine.

A. Screening and Characterization of Mabs

As provided in Table 1, immunization of mice with RT or its subunits as disclosed in the Examples herein resulted in the production of Mabs that recognized either RTA or RTB bound to the solid phase.

TABLE 1

Immunoreactivity of Mab culture fluids by ELISA after secondary screening.

| Immunogen | Mab # | ELISA[1] RTA | ELISA[1] RTB | ELISA[1] RT | Immunoblot[2] RTA | Immunoblot[2] RTB |
|---|---|---|---|---|---|---|
| +Control | anti-RT[3] | ++ | ++ | ++ | + | + |
| RTA | 1E4 | + | + | + | | |
| | 1A5 | ++ | − | + | | |
| | 7A12 | − | + | + | | |
| | 12H2 | − | − | + | | |
| | 7G12 | + | − | ++ | | |
| | 8G2 | ++ | − | ++ | + | + |
| | 1A6 | ++ | − | ++ | | |
| | 10B7 | − | + | + | | |
| | 12F10 | ++ | − | ++ | + | − |
| RTB | 15C5 | − | ++ | ++ | − | − |
| | 11D7 | − | ++ | ++ | − | + |
| | 1H10 | − | − | + | | |
| | 14F11 | − | + | ++ | − | − |
| | 8H10 | − | − | + | | |
| | 9C3 | − | + | ++ | − | + |
| | 6E3 | − | − | − | | |
| | 6B10 | − | + | + | | |
| | 4H3 | − | + | + | | |
| | 1A7 | − | − | − | | |
| RT | 5D1 | − | ++ | ++ | − | + |
| | 3B7 | + | − | ++ | | |
| | 11A12 | + | + | + | − | − |
| | 11E6 | − | − | ++ | | |
| | 9A4 | + | ++ | ++ | − | − |
| | 8G5 | − | − | ++ | | |
| | 3E2 | + | − | ++ | | |
| | 1G8 | + | − | ++ | | |

TABLE 1-continued

Immunoreactivity of Mab culture fluids by ELISA after secondary screening.

| Immunogen | Mab # | ELISA[1] RTA | ELISA[1] RTB | ELISA[1] RT | Immunoblot[2] RTA | Immunoblot[2] RTB |
|---|---|---|---|---|---|---|
| | 11C2 | + | − | ++ | | |
| | 8G8 | − | − | − | | |

[1]Culture fluids were diluted 1:5 and assayed by ELISA as described. Relative immunoreactivity is defined as the following: ++ = $A_{405} > 4$; + = $A_{405} \geqq 1$; − = $A_{405}$ The Mabs may be obtained from hybridomas available from the American Type Culture Collection. Specifically, the Mabs 8G2, 9C3, 11D7, 12F10, 14F11, and 15C5 may be obtained from the hybridomas having ATCC Accession Nos. PTA-6105, PTA-6106, PTA-6107, PTA-6108, PTA-6109, and PTA-6110, respectively, deposited on 23 Jun. 2004 with the American Type Culture Collection, 10801 University Blvd., Manassas, Va. 20110-2209.

In some cases, the Mabs that were raised to a single subunit appeared to recognize RT only. One possible explanation may be that the Mabs have a very weak affinity for the subunit and could only be detected in the ELISA when the subunit was part of the holotoxin, rather than being by itself. Those Mabs that recognized both RT and the subunit used as the immunogen were selected for additional characterization and evaluation. As shown in Table 2, most of the Mabs selected were IgG1κ, with the exception of one clone, 11A12, which appeared to have a mixed isotype, presumably due to being in the process of class switching.

TABLE 2

Evaluation of the utility of selected anti-ricin Mabs for either direct detection or for capture of antigen in an ELISA and by immunoblotting analysis after additional subcloning and affinity purification.[1]

| | | | Specific Activity (U/mg)[2] | | | | | | | |
|---|---|---|---|---|---|---|---|---|---|---|
| | | | Direct[3] | | | | Capture[4] | | Immunoblot[5] | |
| Immunogen | Mab | Isotype | Agg I | RT | RTA | RTB | Agg I | RT | RTA | RTB |
| Control | J010300 | IgG | 0 | 51200 | 12800 | 0 | 0 | 3200 | + | + |
| RTA | 8G2-1-1 | IgG1k | 50 | 25 | 200 | 0 | 0 | 0 | + | + |
| | 12F10-1-1 | IgG1k | 1600 | 800 | 0 | 0 | 0 | 0 | + | − |
| RTB | 15C5-1-1 | IgG1k | 1600 | 12800 | 0 | 0 | 0 | 50 | − | − |
| | 9C3-1-1 | IgG1k | 3200 | 15000 | 0 | 0 | 200 | 400 | − | + |
| | 11D7-1-1 | IgG1k | 0.0 | 800 | 0 | 0 | 0 | 0 | − | + |
| | 14F11-1-1 | IgG1k | 1600 | 3200 | 0 | 0 | 0 | 200 | − | − |
| RT | 11A12-1-1 | Mix: IgMk | 0 | 0 | 0 | 0 | 0 | 0 | − | − |
| | 5D1-1-1 | IgG1k | 0 | 0 | 0 | 0 | 0 | 0 | − | + |
| | 9A4-1-1 | IgG1k | 0 | 0 | 0 | 0 | 0 | 0 | − | − |

[1]Mabs were subcloned and rescreened for their ability to recognize the antigen indicated after affinity purification and concentration.

[2]Specific activity (units/mg) = titer/initial concentration of antibody (mg/ml).

[3]Describes the ability of Mab to directly detect ricin agglutinin I, RT, RTA, and RTB bound to a solid-phase surface.

[4]Mabs were bound to a solid-phase surface and then evaluated for their ability to capture ricin agglutinin I, RT, RTA, and RTB in solution.

[5]Describes immunoreactivity of Mab indicated to either RTA or RTB after electrophoretic separation of the antigen by SDS-PAGE and transfer to a nitrocellulose membrane.

[6]Affinity-purified polyclonal goat anti-RT IgG was used as a positive control.

Tables 3A–3K show the specific concentrations and amounts used in the assay summarized in Table 2.

TABLE 3A

J010300

| Antigen type:<br>Assay Type: | Agg I<br>Direct | Agg II<br>Direct | Agg I<br>Capture | Agg II<br>Capture | A Chain<br>Direct | B Chain<br>Direct |
|---|---|---|---|---|---|---|
| Volume (ml) | 1.0 | 1.0 | 1.0 | 1.0 | 1.0 | 1.0 |
| Protein conc. (mg/ml) | 4.8 | 4.8 | 4.8 | 4.8 | 4.8 | 4.8 |
| Total protein (mg) | 4.8 | 4.8 | 4.8 | 4.8 | 4.8 | 4.8 |
| ELISA Titer | 0 | 1024 | 0 | 128 | 512 | 0 |
| ELISA Ab starting concentration (mg/ml) | 0.04 | 0.02 | 0.04 | 0.04 | 0.04 | 0.04 |
| Specific activity (U/mg) | 0 | 51200 | 0 | 3200 | 12800 | 0 |
| Total activity (U) | 0 | 245760 | 0 | 15360 | 61440 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3B

8G2-1-1

| Antigen type:<br>Assay Type: | Agg I<br>Direct | Agg II<br>Direct | Agg I<br>Capture | Agg II<br>Capture | A Chain<br>Direct | B Chain<br>Direct |
|---|---|---|---|---|---|---|
| Volume (ml) | 1.0 | 1.0 | 1.0 | 1.0 | 1.0 | 1.0 |
| Protein conc. (mg/ml) | 3.58 | 3.58 | 3.58 | 3.58 | 3.56 | 3.56 |
| Total protein (mg) | 3.6 | 3.6 | 3.6 | 3.6 | 3.6 | 3.6 |
| ELISA Titer | 2 | 1 | 0 | 0 | 8 | 0 |
| ELISA Ab starting concentration (mg/ml) | 0.04 | 0.04 | 0.04 | 0.04 | 0.04 | 0.04 |
| Specific activity (U/mg) | 50 | 25 | 0 | 0 | 200 | 0 |
| Total activity (U) | 179 | 90 | 0 | 0 | 712 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3C

12F10-1-1

| Antigen type:<br>Assay Type: | Agg I<br>Direct | Agg II<br>Direct | Agg I<br>Capture | Agg II<br>Capture | A Chain<br>Direct | B Chain<br>Direct |
|---|---|---|---|---|---|---|
| Volume (ml) | 1.0 | 1.0 | 1.0 | 1.0 | 1.0 | 1.0 |
| Protein conc. (mg/ml) | 1.22 | 1.22 | 1.22 | 1.22 | 1.22 | 1.22 |
| Total protein (mg) | 1.2 | 1.2 | 1.2 | 1.2 | 1.2 | 1.2 |
| ELISA Titer | 64 | 32 | 0 | 0 | 0 | 0 |
| ELISA Ab starting concentration (mg/ml) | 0.04 | 0.04 | 0.04 | 0.04 | 0.04 | 0.04 |
| Specific activity (U/mg) | 1600 | 800 | 0 | 0 | 0 | 0 |
| Total activity (U) | 1952 | 976 | 0 | 0 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3D

15C5-1-1

| Antigen type:<br>Assay Type: | Agg I<br>Direct | Agg II<br>Direct | Agg I<br>Capture | Agg II<br>Capture | A Chain<br>Direct | B Chain<br>Direct |
|---|---|---|---|---|---|---|
| Volume (ml) | 1.0 | 1.0 | 1.0 | 1.0 | 1.0 | 1.0 |
| Protein conc. (mg/ml) | 0.83 | 0.83 | 0.83 | 0.83 | 0.83 | 0.83 |
| Total protein (mg) | 0.8 | 0.8 | 0.8 | 0.8 | 0.8 | 0.8 |
| ELISA Titer | 64 | 512 | 0 | 2 | 0 | 0 |

TABLE 3D-continued

15C5-1-1

| Antigen type: Assay Type: | Agg I Direct | Agg II Direct | Agg I Capture | Agg II Capture | A Chain Direct | B Chain Direct |
|---|---|---|---|---|---|---|
| ELISA Ab starting concentration (mg/ml) | 0.04 | 0.04 | 0.04 | 0.04 | 0.04 | 0.04 |
| Specific activity (U/mg) | 1600 | 12800 | 0 | 50 | 0 | 0 |
| Total activity (U) | 1328 | 10624 | 0 | 42 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3E

9C3-1-1

| Antigen type: Assay Type: | Agg I Direct | Agg II Direct | Agg I Capture | Agg II Capture | A Chain Direct | B Chain Direct |
|---|---|---|---|---|---|---|
| Volume (ml) | 1.0 | 1.0 | 1.0 | 1.0 | 1.0 | 1.0 |
| Protein conc. (mg/ml) | 1.23 | 1.23 | 1.23 | 1.23 | 1.23 | 1.23 |
| Total protein (mg) | 1.2 | 1.2 | 1.2 | 1.2 | 1.2 | 1.2 |
| ELISA Titer | 128 | 600 | 8 | 16 | 0 | 0 |
| ELISA Ab starting concentration (mg/ml) | 0.04 | 0.04 | 0.04 | 0.04 | 0.04 | 0.04 |
| Specific activity (U/mg) | 3200 | 15000 | 200 | 400 | 0 | 0 |
| Total activity (U) | 3936 | 18450 | 246 | 492 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3F

11D7-1-1

| Antigen type: Assay Type: | Agg I Direct | Agg II Direct | Agg I Capture | Agg II Capture | A Chain Direct | B Chain Direct |
|---|---|---|---|---|---|---|
| Volume (ml) | 1.0 | 1.0 | 1.0 | 1.0 | 1.0 | 1.0 |
| Protein conc. (mg/ml) | 1.12 | 1.12 | 1.12 | 1.12 | 1.12 | 1.12 |
| Total protein (mg) | 1.1 | 1.1 | 1.1 | 1.1 | 1.1 | 1.1 |
| ELISA Titer | 0 | 32 | 0 | 0 | 0 | 0 |
| ELISA Ab starting concentration (mg/ml) | 0.04 | 0.04 | 0.04 | 0.04 | 0.04 | 0.04 |
| Specific activity (U/mg) | 0.0 | 800 | 0 | 0 | 0 | 0 |
| Total activity (U) | 0 | 896 | 0 | 0 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3G

14F11-1-1

| Antigen type: Assay Type: | Agg I Direct | Agg II Direct | Agg I Capture | Agg II Capture | A Chain Direct | B Chain Direct |
|---|---|---|---|---|---|---|
| Volume (ml) | 1.0 | 1.0 | 1.0 | 1.0 | 1.0 | 1.0 |
| Protein conc. (mg/ml) | 1.48 | 1.48 | 1.48 | 1.48 | 1.48 | 1.48 |
| Total protein (mg) | 1.5 | 1.5 | 1.5 | 1.5 | 1.5 | 1.5 |
| ELISA Titer | 64 | 128 | 0 | 8 | 0 | 0 |
| ELISA Ab starting concentration (mg/ml) | 0.04 | 0.04 | 0.04 | 0.04 | 0.04 | 0.04 |
| Specific activity (U/mg) | 1600 | 3200 | 0 | 200 | 0 | 0 |

TABLE 3G-continued

14F11-1-1

| Antigen type: | Agg I | Agg II | Agg I | Agg II | A Chain | B Chain |
|---|---|---|---|---|---|---|
| Assay Type: | Direct | Direct | Capture | Capture | Direct | Direct |
| Total activity (U) | 2368 | 4736 | 0 | 296 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3H

11A12-1-1

| Antigen type: | Agg I | Agg II | Agg I | Agg II | A Chain | B Chain |
|---|---|---|---|---|---|---|
| Assay Type: | Direct | Direct | Capture | Capture | Direct | Direct |
| Volume (ml) | 1.0 | 1.0 | 1.0 | 1.0 | 1.0 | 1.0 |
| Protein conc. (mg/ml) | 1.33 | 1.33 | 1.33 | 1.33 | 1.33 | 1.33 |
| Total protein (mg) | 1.3 | 1.3 | 1.3 | 1.3 | 1.3 | 1.3 |
| ELISA Titer | 0 | 0 | 0 | 0 | 0 | 0 |
| ELISA Ab starting concentration (mg/ml) | 0.04 | 0.04 | 0.04 | 0.04 | 0.04 | 0.04 |
| Specific activity (U/mg) | 0 | 0 | 0 | 0 | 0 | 0 |
| Total activity (U) | 0 | 0 | 0 | 0 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3I

5D1-1-1

| Antigen type: | Agg I | Agg II | Agg I | Agg II | A Chain | B Chain |
|---|---|---|---|---|---|---|
| Assay Type: | Direct | Direct | Capture | Capture | Direct | Direct |
| Volume (ml) | 1.0 | 1.0 | 1.0 | 1.0 | 1.0 | 1.0 |
| Protein conc. (mg/ml) | 0.707 | 0.707 | 0.707 | 0.707 | 0.707 | 0.707 |
| Total protein (mg) | 0.7 | 0.7 | 0.7 | 0.7 | 0.7 | 0.7 |
| ELISA Titer | 0 | 0 | 0 | 0 | 0 | 0 |
| ELISA Ab starting concentration (mg/ml) | 0.04 | 0.04 | 0.04 | 0.04 | 0.04 | 0.04 |
| Specific activity (U/mg) | 0 | 0 | 0 | 0 | 0 | 0 |
| Total activity (U) | 0 | 0 | 0 | 0 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3J

9A4-1-1

| Antigen type: | Agg I | Agg II | Agg I | Agg II | A Chain | B Chain |
|---|---|---|---|---|---|---|
| Assay Type: | Direct | Direct | Capture | Capture | Direct | Direct |
| Volume (ml) | 1.0 | 1.0 | 1.0 | 1.0 | 1.0 | 1.0 |
| Protein conc. (mg/ml) | 0.287 | 0.287 | 0.287 | 0.287 | 0.287 | 0.287 |
| Total protein (mg) | 0.3 | 0.3 | 0.3 | 0.3 | 0.3 | 0.3 |
| ELISA Titer | 0 | 0 | 0 | 0 | 0 | 0 |
| ELISA Ab starting concentration (mg/ml) | 0.04 | 0.04 | 0.04 | 0.04 | 0.04 | 0.04 |
| Specific activity (U/mg) | 0 | 0 | 0 | 0 | 0 | 0 |
| Total activity (U) | 0 | 0 | 0 | 0 | 0 | 0 |
| Detector Used | | | R1254 Rbt | R1254 Rbt | | |

Specific activity = Titer (recip. of dilution)/starting Ab concentration (in first well)
Total activity = Specific activity × Mass

TABLE 3K

ELISA Capture with Mabs

| Antibody 1 | Antibody 2 | Antibody 3 | Antibody 4 | Conc. Used ug/ml | Assay Sensitivity Agg I ng/ml | Agg II ng/ml |
|---|---|---|---|---|---|---|
| 12F10-1-1 | | | | 10.0 | <20 | <20 |
| 15C5-1-1 | | | | 10.0 | <20 | <20 |
| 9C3-1-1 | | | | 2.5 | 20.00 | 2.50 |
| 9C3-1-1 | | | | 10.0 | 10.00 | 2.50 |
| J010300 | | | | 2.5 | 10.00 | 1.25 |
| J010300 | | | | 10.0 | 5.00 | 0.63 |
| J010300 | 9C3-1-1 | | | 10 Each | 2.50 | 1.25 |
| J010300 | 9C3-1-1 | 12F10-1-1 | | 10 Each | 20.00 | 2.50 |
| J010300 | 9C3-1-1 | 12F10-1-1 | 15C5-1-1 | 10 Each | 20.00 | 2.50 |
| J010300 | 9C3-1-1 | 12F10-1-1 | 15C5-1-1 | 2.5 Each | 5.00 | 1.25 |

Several of the Mabs appeared to be unable to recognize either RTA or RTB in a Western blot, even though they were able to recognize RT in an ELISA. This suggests that these clones might recognize conformational epitopes that are denatured when the toxin is separated by SDS-PAGE.

B. Mabs as Immundiagnostic Reagents

As disclosed in the Examples, several of the Mabs were evaluated for their ability to be used as immunodiagnostic reagents in a solid-phase immunoassay. The Mabs were evaluated for their ability to recognize RT, RTA, RTB, and Ricin communis agglutinin I (RCA 120), which is closely related to RT (Ricin communis agglutinin II, RCA 60). See Sweeney & Tonevitsky (1997) Proteins 28(4):586–589, which is herein incorporated by reference. The Mabs were evaluated for their ability to be used both as a capture reagent, when bound to the solid phase, and as a detection reagent when the antigen was immobilized. Several of the Mabs were able to detect the presence of both RT and agglutinin I when bound to the solid phase. See Table 3. This confirms findings in the literature that the subunits of agglutinin I are highly homologous to RT. Interestingly, the Mabs raised to RTB were much more effective than those raised to RTA at detecting RT bound to the solid phase. This may suggest that epitopes encoded by RTB are more exposed than those on RTA when the holotoxin is bound to the solid phase.

With the exception of clones 15C5, 9C3, and 14F11, most of the Mabs were not able to capture antigen when bound to the solid-phase. See Table 3. These clones were RTB-specific Mabs that could weakly capture RT from solution. In addition, none of the Mabs were able to detect either RTA or RTB when bound to the solid phase, with the exception of clone 8G2, that recognized RTA. The relative inability of these Mabs to capture antigen when bound to the solid phase suggested that they may be too constrained to interact well with their cognate antigen.

C. Neutralization of RT

The ability of the Mabs to inhibit RT-induced eukaryotic cell cytotoxicity in vitro was determined by two different methods as disclosed in the Examples below. In the first method, the Mabs were evaluated for their ability to inhibit RT-induced cytotoxicity in murine EL-4 cells, using Alamar blue (Biosource International, Camarillo, Calif.) as a vital stain to quantify cell death. See O'Brien, J., et al. (2000) Eur. J. Biochem. 267:5421–6, which is herein incorporated by reference. Based on this methodology, several of the Mabs were able to inhibit EL-4 cell cytotoxicity as shown in FIG. 1.

Although both RTA- and RTB-specific Mabs were able to inhibit cytotoxicity, the Mabs that were most effective in inhibiting cytotoxicity were those raised against RTB, thereby indicating that inhibiting the binding of RT to the cell is more effective in treating or preventing cytotoxicity.

As an alternative method, the RTB-specific Mabs clones 9C3 and 11D7 were evaluated for their ability to inhibit RT-induced cytotoxicity in primary cultures of human lung epithelium. The results are shown in Table 4.

TABLE 4

Ability of selected Mabs to protect human lung epithelial cells against ricin intoxication in vitro[1]

| Immunogen | Mab | Protective Concentration[2] (nM) |
|---|---|---|
| Control | Goat anti-RT | <0.006 |
| RTB | 9C3-1-1 | 33 |
| RTB | 11D7-1-1 | 27 |

[1]Primary human lung epithelial cells were exposed in culture to an $ED_{70}$ (7 pM) of RT.
[2]Calculated on the basis of the expected maximum yield of Mab in solution (50 μg/ml).

Both Mabs were similar in their ability to inhibit cytotoxicity in vitro, although they were 1000-fold less effective than the affinity-purified polyclonal goat anti-RT which was used as a positive control. Therefore, in some embodiments of the present invention, a mixture comprising a plurality of Mabs which recognize a plurality of epitopes may be used to compensate or overcome this poor efficacy (relative to polyclonal sera). It should be noted that, the Mabs may be selected for desired activity, e.g. recognition of certain epitopes, by those skilled in the art using methods known in the art. In addition, one skilled in the art may use known methods, such as affinity maturation, in order to improve the affinity and avidity of the Mabs for their cognate antigen.

Therefore, the present invention provides Mabs that may be used as reagents for assaying, detecting, measuring, or monitoring the presence of RT. The Mabs of the present invention may also be employed in pharmaceutical compositions and methods for treating, preventing, inhibiting, or modulating RT-induced intoxication in a subject. In some embodiments, at least one Mab may be administered to a subject prior to exposure of risk of exposure to ricin toxin in order to provide prophylactic protection against ricin intoxication.

As used herein, "antibody" includes whole antibodies and any antigen binding fragment, i.e. "antigen-binding portion" or single chain thereof. An "antibody" refers to a glycoprotein comprising at least two heavy (H) chains and two light (L) chains inter-connected by disulfide bonds, or an antigen binding portion thereof. Each heavy chain comprises a heavy chain variable region ($V_H$) and a heavy chain constant region. The heavy chain constant region comprises three domains, $C_{H1}$, $C_{H2}$ and $C_{H3}$. Each light chain comprises a light chain variable region ($V_L$) and a light chain constant region. The light chain constant region comprises one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system, e.g. effector cells, and the first component (Clq) of the classical complement system.

As used herein, "antigen-binding portion" of an antibody or alternatively, "antibody portion", refers to one or more fragments of an antibody that retain the ability to bind to an antigen, e.g. RT. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_H$, domains; (iv) a Fv fragment consisting of the $V_L$ and $V_H$ domains of a single arm of an antibody, (v) a dAb fragment, which comprises a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g. Bird et al. (1988) Science 242:423–426; and Huston et al. (1988) PNAS USA 85:5879–5883, which are herein incorporated by reference. Such single chain antibodies are also intended to be encompassed within the term "antigen-binding portion" of an antibody. These antibody fragments are obtained using methods known in the art, and the fragments are screened for activity in the same manner as are intact antibodies.

As used herein, "epitope" refers to a protein determinant capable of specific binding to an antibody. Epitopes usually comprise chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, "monoclonal antibody" refers to a antibody molecules of single molecular composition. Accordingly, the term "human monoclonal antibody" refers to antibodies displaying a single binding specificity which have variable and constant regions derived from human germ-line immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light chain transgene fused to an immortalized cell.

As used herein, an "isolated antibody" refers to an antibody which is substantially free of other antibodies having different antigenic specificities, e.g. an isolated antibody that binds to RT is substantially free of antibodies that bind antigens other than RT. An isolated antibody that binds to an epitope, isoform or variant of RT may, however, have cross-reactivity to other related antigens, e.g. from other species such as RTA and RTB. Moreover, an isolated antibody may be substantially free of other cellular material and/or chemicals. In some embodiments, the present invention provides a combination of "isolated" monoclonal antibodies which have different antigenic specificities.

As used herein, "specific binding" refers to antibody binding to a predetermined antigen. Typically, the antibody binds with an affinity of at least about $1 \times 10^7$ $M^{-1}$, and binds to the predetermined antigen with an affinity that is at least about two-fold greater than its affinity for binding to a non-specific antigen, e.g. BSA or casein, other than the predetermined antigen or a closely-related antigen. As used herein, the phrases "an antibody recognizing an antigen", "an antibody against an antigen", or "an antibody specific for an antigen" are used interchangeably with the phrase "an antibody which binds specifically to an antigen".

As used herein, "high affinity" for an IgG antibody refers to a binding affinity of at least about $10^7$ $M^{-1}$, preferably at least about $10^8$ $M^{-1}$, more preferably at least about $10^9$ $M^{-1}$, $10^{10}$ $M^{-1}$, $10$ $M^{-1}$ or greater, e.g., up to $10^{13}$ $M^{-1}$ or greater. However, "high affinity" binding can vary for other antibody isotypes. For example, "high affinity" binding for an IgM isotype refers to a binding affinity of at least about $1 \times 10^7$ $M^{-1}$.

The Mabs of the present invention can be produced by a variety of techniques, including known monoclonal antibody methodologies, e.g. somatic cell hybridization techniques of Kohler and Milstein (1975) Nature 256:495, which is herein incorporated by reference. Although somatic cell hybridization procedures are preferred, in principle, other techniques for producing monoclonal antibody can be employed, e.g. viral or oncogenic transformation of B lymphocytes.

The preferred animal system for preparing hybridomas is the murine system. Hybridoma production in the mouse is known in the art. Immunization protocols and techniques for isolation of immunized splenocytes for fusion are known in the art. Fusion partners, e.g. murine myeloma cells, and fusion procedures are also known.

Somatic cells with the potential for producing antibody and, in particular B lymphocytes, are suitable for fusion with a B-cell myeloma line using methods known in the art. Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. Once-primed or hyperimmunized animals can be used as a source of antibody-producing lymphocytes. Mice, rats, rabbits, hamsters, sheep, frogs and the like may also be used as hosts for preparing antibody-producing cells using methods known in the art. See Monoclonal Antibodies: Principles and Practice, 2d ed., Orlando, Fla., Academic Press, 1986, which is herein incorporated by reference. Alternatively, human somatic cells capable of producing antibody, specifically B lymphocytes, are suitable for fusion with myeloma cell lines using methods known in the art.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Such myeloma cell lines are known in the art and include P3-X63/Ag8, X63-Ag8.653, NS1/1.Ag 4.1, Sp210-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans, and the like. See Monoclonal Antibodies: Principles and Practice, 2d ed., pp. 65–66, Orlando, Fla., Academic Press, 1986; and Monoclonal Antibody Technology, Laboratory Techniques in Biochemistry and Molecular Biology, vol. 13, Burden and Von Knippenberg, eds. pp. 75–83, Amsterdam, Elsevier, 1984, which are herein incorporated by reference.

Monoclonal antibodies or purified fragments of the monoclonal antibodies having at least a portion of an antigen binding region, including such as Fv, F(ab')$_2$, Fab fragments, single chain antibodies, chimeric or humanized antibodies and complementarity determining regions (CDR) may be prepared by methods known in the art. See Harlow & Lane (1988) Antibody, Cold Spring Harbor; U.S. Pat. No. 4,946,778; Morrison et al. (1984) PNAS USA 81:6851; and Newuberger et al. (1984) Nature 81:6851, which are herein incorporated by reference. Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, and the like.

The Mabs of the present invention may be used as antidotes for ricin intoxication. See Lemley, et al. (1994) Hybridoma 13(5):417–427 and U.S. Pat. No. 5,626,844, which are herein incorporated by reference. The Mabs of the present invention may be used to prevent or treat systemic side effects of locally administered ricin toxin.

Antibodies of the present invention may be produced by conventional methods known in the art. See e.g., Coligan (1991) CURRENT PROTOCOLS IN IMMUNOLOGY. Wiley/Greene, N.Y.; and Harlow & Lane (1989) ANTIBODIES: A LABORATORY MANUAL, Cold Spring Harbor Press, NY; Stites, et al. (1986) BASIC AND CLINICAL IMMUNOLOGY. 4th ed. Lange Medical Publications, Los Altos, Calif.; Goding (1986) MONOCLONAL ANTIBODIES: PRINCIPLES AND PRACTICE. 2d ed. Academic Press, New York, N.Y.; and Kohler & Milstein (1975) Nature 256:495–497, which are herein incorporated by reference. Therapeutic antibodies may be produced specifically for clinical use in humans by conventional methods known in the art. See Chadd & Chamow (2001) Curr. Opin. Biotechnol. 12:188–194 and references therein, all of which are herein incorporated by reference.

As used herein, "antibody" refers to immunoglobulin molecules and immunologically active portions that comprise an antigen binding site which specifically binds an antigen, such as ricin. Examples of immunologically active portions of immunoglobulin molecules include F(ab) and F(ab')$_2$ fragments which may be generated by treating the antibody with an enzyme such as pepsin. Polyclonal and monoclonal antibodies against the polypeptides of the present invention may be made by conventional methods known in the art.

The Mabs of the present invention may be administered, preferably in the form of pharmaceutical compositions, to a subject. Preferably the subject is mammalian, more preferably, the subject is human. Preferred pharmaceutical compositions are those comprising at least one Mab against RT, RTA, RTB, or a combination thereof in a therapeutically effective amount, and a pharmaceutically acceptable vehicle. The immunogenic composition may elicit an immune response that need not be protective or the immunogenic composition may provide passive immunity. Methods known in the art may be used to determine the feasibility of using the Mabs of the present invention for treating, preventing, inhibiting, or modulating ricin intoxication. A protective immune response may be complete or partial, i.e. a reduction in symptoms as compared with a control.

The present invention also provides compositions, including pharmaceutical compositions, which comprise at least one of the Mabs described herein or an antigen-binding portion thereof and a carrier such as a pharmaceutically acceptable carrier. In some embodiments, the compositions comprise a plurality of Mabs or antigen-binding portions thereof of the invention. In some embodiments, each of the Mabs or antigen-binding portions thereof of the composition binds to different epitopes on RTA, RTB, RT, or a combination thereof.

The compositions of the present invention may be used to treat, prevent, or inhibit ricin intoxication. The compositions of the invention may be used in combination therapies. For example, the pharmaceutical compositions of the present invention may be administered to a subject in combination or in conjunction with other agents useful for treating, preventing, inhibiting, or modulating intoxication from other toxins, injuries due to exposure to chemical and biological warfare agents. For example, the compositions of the present invention may be administered with antibodies against botulinum toxin, antibodies or antibiotics against *Bacillus anthracis*, and the like.

The pharmaceutical compositions may include an adjuvant. As used herein, an "adjuvant" refers to any substance which, when administered with or before the polypeptide, polynucleotide, or antibody of the present invention, aids the polypeptide, polynucleotide, or antibody in its mechanism of action. Thus, an adjuvant in a vaccine is a substance that aids the immunogenic composition in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by methods known in the art.

In accordance with the present invention, at least one Mab may be administered in a therapeutically effective amount to a mammal such as a human. A therapeutically effective amount may be readily determined by standard methods known in the art. As used herein, a "therapeutically effective amount" of a Mab according to the present invention is an amount that treats, prevents, or inhibits ricin intoxication as compared to a control using methods known in the art. The skilled artisan will appreciate that certain factors may influence the dosage required to effectively treat a subject, including but not limited to the severity of ricin exposure/intoxication, previous treatments, the general health and/or age of the subject, other diseases present, and infection, intoxication or exposure to other toxins, bacteria, or chemicals. Preferred effective amounts of the Mabs of the invention ranges from about 1 to about 500 mg/kg body weight, preferably about 1 to about 250 mg/kg body weight, more preferably about 1 to about 100 mg/kg body weight.

Moreover, treatment of a subject with a Mab or composition of the present invention can include a single treatment or, preferably, can include a series of treatments. The Mabs and compositions of the present invention may be administered to a subject before, during, after or a combination thereof ricin exposure. The Mabs and compositions of the present invention may be administered prior to possible exposure to ricin. It will also be appreciated that the effective dosage of the compound used for treatment may increase or decrease over the course of a particular treatment. Changes in dosage may result and become apparent by standard diagnostic assays known in the art. In some conditions, chronic administration may be required.

The pharmaceutical compositions of the present invention may be provided in a dosage unit form appropriate for the desired mode of administration. As used herein, "dosage unit form" refers to physically discrete units suited as unitary dosages for the subject to be treated; each unit containing a predetermined quantity of active compound calculated to produce the desired therapeutic effect in association with the required pharmaceutical carrier.

The Mabs of the invention can be incorporated into pharmaceutical compositions suitable for administration. Pharmaceutical compositions of this invention comprise a therapeutically effective amount of at least one Mab disclosed herein, and an inert, pharmaceutically acceptable carrier or diluent. Preferred amounts of the Mabs of the present invention range from about 1 to about 10,000 µg per single dose.

As used herein, a "pharmaceutically acceptable vehicle" or "pharmaceutically acceptable carrier" refers to and includes any and all solvents, dispersion media, coatings, antibacterial and antifungal agents, isotonic and absorption delaying agents, and the like, that are compatible with pharmaceutical administration. Pharmaceutically acceptable vehicles include those known in the art. See e.g. REMINGTON: THE SCIENCE AND PRACTICE OF PHARMACY. 20$^{th}$ ed. (2000) Lippincott Williams & Wilkins. Baltimore, Md., which is herein incorporated by reference.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art. Except insofar as any conventional media or agent is incompatible with the Mabs disclosed herein, use thereof in the compositions is contemplated.

Supplementary active compounds can also be incorporated into the compositions. Supplementary active compounds include those known in the art for treating, preventing, or inhibiting injuries and intoxications caused by chemical and biological warfare agents. Supplementary active compounds and treatments include those provided in the PDR GUIDE TO BIOLOGICAL AND CHEMICAL WARFARE RESPONSE: DIAGNOSIS, TREATMENT, PREVENTION by Medical Economics with foreword by John G. Bartlett (2002), MEDICAL MANAGEMENT OF BIOLOGICAL CASUALTIES HANDBOOK, 4th ed. (2001) U.S. Army Medical Research Institute of Infectious Diseases, Fort Detrick, Md., and MEDICAL ASPECTS OF CHEMICAL AND BIOLOGICAL WARFARE (1997) Office of the Surgeon General at TMM Publications Borden Institute, Walter Reed Army Medical Center, Washington, D.C. 20307-5001, which are herein incorporated by reference. Supplementary compounds include vaccines, antibiotics, antidotes and the like, such as Bioport™ (Bioport Corporation, Lansing, Mich.), ciprofloxacin, gentamicin, erythromycin, chloramphenicol, doxycycline, penicillin, tetracycline, norfloxacin, streptomycin, trimethoprim-sulfamethoxazole, rifampin, ofloxacin, cidofovir, CDC trivalent equine antitoxin, ribavirin, atropine, pralidoxime, amyl nitrate, sodium nitrate, sodium thiosulfate, and the like.

The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient and the given Mab. Certain administration routes may be preferred according to the mode of ricin exposure. For example, for treating exposure to ricin via inhalation, the preferred route of administration of the Mabs or compositions of the present invention may be inhalation. Similarly, for treating exposure to ricin via injection, the preferred route of administration may be injection at the site of the ricin injection.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

The compositions of the invention may be manufactured in manners generally known for preparing pharmaceutical compositions, e.g., using known techniques such as mixing, dissolving, granulating, dragee-making, levigating, emulsifying, encapsulating, entrapping or lyophilizing. Pharmaceutical compositions may be formulated according to methods known in the art using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the Mab with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating at least one polyphenolic compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Depending on the route of administration, the Mabs of the present invention may be coated in a material to protect the Mabs from the action of acids and other natural conditions that may inactivate the Mabs. For example, the Mab may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes. See Strejan et al. (1984) J. Neuroimmunol. 7:27, which is herein incorporated by reference.

In some embodiments, the Mabs are prepared with carriers that will protect against rapid release and/or rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. Many methods for the preparation of such formulations are patented or generally known to those skilled in the art. See e.g. U.S. Pat. No. 4,522,811; and SUSTAINED AND CONTROLLED RELEASE DRUG DELIVERY SYSTEMS, J. R. Robinson, ed., Marcel Dekker, Inc., New York (1978), which are herein incorporated by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

It will be appreciated that the actual dosages of the Mabs used in the compositions of this invention will vary according to the particular Mab being used, the particular composition formulated, the mode of administration, and the particular site, host, and type of exposure/intoxication being treated. Optimal dosages for a given set of conditions may be ascertained by those skilled in the art using dosage-determination tests known in the art in view of the experimental data for a given Mab.

In certain embodiments, the Mabs of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes using methods known in the art. See e.g., U.S. Pat. Nos. 4,522,811; 5,374,548; and 5,399,331, which are herein incorporated by reference. The liposomes may comprise one or more moieties which are selectively transported into specific cells or organs, thereby enhancing targeted drug delivery. See e.g., Ranade, V.V. (1989) J. Clin. Pharmacol. 29:685; U.S. Pat. No. 5,416,016; Umezawa et al. (1988) Biochem. Biophys. Res. Commun. 153:1038; Bloeman et al. (1995) FEBS Lett. 357:140; Owais et al. (1995) Antimicrob. Agents Chemother. 39:180; Briscoe et al. (1995) Am. J. Physiol. 1233:134; Schreier et al. (1994) J. Biol. Chem. 269:9090); Keinanen & Laukkanen (1994) FEBS Lett. 346:123; Killion & Fidler (1994) Immunomethods 4:273, which are herein incorporated by reference. In some embodiments of the invention, the Mabs are formulated in liposomes. The liposomes may include a targeting moiety. In some embodiments, the Mabs in the liposomes are delivered by bolus injection to a site proximal to the desired area, e.g. the site of inflammation or infection or exposure.

The Mabs and compositions of the present invention can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556, which are herein incorporated by reference. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Toxicity and therapeutic efficacy of such compounds can be determined by standard pharmaceutical procedures in cell cultures or experimental animals. For example, one may determine the lethal dose of toxin, $LCt_{50}$ (the dose expressed as concentration of toxin×exposure time that is lethal to 50% of the population) or the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The present invention also provides Mabs or compositions of the present invention may be provided in kits along with instructions for use. Kits according to the present invention may contain least one Mab or a pharmaceutical composition comprising at least one Mab as a single dose or multiple doses. The kit may include a device for delivering the Mab or pharmaceutical composition. The device may be a multi-chambered syringe for intramuscular delivery, a microneedle or set of microneedle arrays for transdermal delivery, a small balloon for intranasal delivery, or a small aerosol generating device for delivery by inhalation.

Ricin exposure is presently detected by medical history and symptoms, and is confirmed by antibody- or activity-based measurements of ricin in bodily fluids. Ricin detection or medical diagnosis of ricin exposure, therefore, may based upon immunoassays utilizing the Mabs of the present invention.

The present invention also provides kits for conducting the assays described herein. Kits of the present invention comprise the Mabs of the present invention packaged together with other reagents used for conducting the assays described herein, devices for obtaining the samples to be assayed, devices for mixing the reagents and conducting the assays, instructional material, or a combination thereof. The diagnostic assays may be provided in the form of kits that may be used outside of a laboratory setting, such as in the field.

The Mabs may be used to identify the neutralizing epitopes of ricin and its subunits using methods known in the art in order to develop vaccines and drugs that specifically recognize these areas of the toxin and either inhibit the enzymatic activity of ricin and/or its ability to bind to cells and be internalized.

The complementary-determining regions (CDR) of the immunoglobulin genes of the hybridoma cell lines may be mapped using methods known in the art to determine the specific amino acid sequence of the critical antigen-binding domain of the Mabs of the present invention and generate information that may be used to engineer improved Mabs.

The following Examples are intended to illustrate, but not to limit the present invention.

EXAMPLE 1

Immunizations

Male Balb/c mice, about 3 to about 5 weeks old, were purchased from the National Cancer Institute Frederick Cancer Research Facility (NCI-FCRC), Frederick Md. Purified RTA (Lot #39H4053) and RTB (Lot #64H4084) were purchased from Sigma Chemical Co., St. Louis, Mo. Ricin toxin (Lot #9234) was purchased from Inland Chemical Co., Inland, Tex. Ricin communis agglutinin I (RCA 120) was purchased from Vector Laboratories, Burlingame, Calif.

Mice were primed intraperitoneally (i.p.) with 0.01 µg antigen diluted in phosphate-buffered saline (PBS, pH 7.4, Invitrogen, Carlsbad, Calif.) and emulsified in an equal volume of complete Freund's Adjuvant (BD Biosciences, Sparks, Md.). At two week intervals, the mice were injected i.p. with the following amounts of antigen, emulsified in an equal volume of incomplete Freund's Adjuvant (BD Biosciences, Sparks, Md.): 0.1 µg, 1.0 µg, 10 µg. Two weeks after the last inoculation, serum samples from the mice were evaluated by enzyme-linked immunosorbent assay (ELISA) for reactivity to the immunogen.

EXAMPLE 2

Cell Fusions

Single-cell suspensions, prepared from spleens that had been aseptically removed from immunized mice, were fused with P3X63Ag8.653 myeloma cells (CRL-158–0, American Type Culture Collection, Manassas, Va.) at a 1:2 ratio in 50% (v/v) polyethylene glycol 1500 MW (Boehringer-Mannheim, Indianapolis, Ind.) using methods known in the art. The fused cells were plated in a 96-well microdilution plate and cultured in OptiMEM medium (Invitrogen, Carlsbad, Calif.) containing hypoxanthine, aminopterin, and thymidine (Boehringer-Mannheim) for 14 days to select for antibody producing cells. The cells were cloned by limiting dilution and then the clones were individually expanded. During the cloning procedure, samples of the culture medium were removed and used to screen for the presence of ricin-specific antibody. Clones positive for antibody to ricin were selected for an additional cycle of cloning by limiting dilution and screening prior to expansion.

EXAMPLE 3

Antibody Screening

Samples of culture fluid from each well were screened for the presence of Mabs specific for either holotoxin, RTA, and RTB. Antigen (100 ng/well) was coated onto 96-well U-bottom polyvinyl microtiter plates (BD Biosciences) and incubated 17 hours at 4° C. The plates were washed in PBS containing 0.05% Tween 20 (Sigma) and then blocked for 1 hour with PBS containing 1% bovine serum albumin (BSA, Sigma). The culture fluid was serially diluted 5-fold in PBS+1% BSA and incubated for 2 hours at room temperature. After washing with PBS+1% Tween, the plates were incubated for 2 hours at room temperature with phosphatase-labeled goat anti-mouse IgG (Kirkegaard & Perry Laboratories, Gaithersburg, Md.) diluted 1:250 in PBS+1% BSA. The plates were washed with PBS+1% Tween and developed at room temperature using liquid phosphatase substrate (Sigma, St. Louis, Mo.). The $A_{405}$ of each well was determined using a microplate reader (Molecular Devices, Sunnyvale, Calif.).

EXAMPLE 4

Production and Characterization of Mabs

Hybridoma lines of interest were grown in Integra 1000 flasks (Integra Biosciences, Ijamsville, Md.) using Gibco Hybridoma Serum-Free Medium (Invitrogen, Carlsbad, Calif.) according to the manufacturer's directions. Mab in the culture fluid was precipitated with 30% $NH_4SO_4$ and resuspended in phosphate buffered saline, pH 7.4 (Invitrogen, Carlsbad, Calif.). The Mab was column purified using a protein A affinity column (Pierce Chemcial Co, Rockford, Ill.) after which protein concentration was quantitated by a BCA assay (Pierce Chemical Co, Rockford, Ill.).

EXAMPLE 5

Immunoblotting Analysis

Polyacrylamide gel electrophoresis (SDS-PAGE) and Western blot transfers were performed with a NuPAGE system (Invitrogen) using methods known in the art. NuPAGE 4–12% Bis-Tris gels and MOPS SDS running buffer, following manufacturer's protocol for reduced sample electrophoresis, were used. Ricin, diluted to 30 µg/ml and mixed with sample buffer containing reducing agent was heated at 70° C. for 10 minutes immediately prior to electrophoresis. Proteins from gels were electrophoretically transferred onto nitrocellulose membranes. After transfer, membranes were incubated in PBS containing 5% powdered skim milk (PBS-5M) overnight (4° C.). The membranes were cut into strips containing a lane with ricin protein and Mabs, diluted to 10 µg in 15 ml PBS containing 0.1% Tween 20 (PBST) and 3% skim milk, were incubated for 2 hours at 25° C. The membranes were washed in PBST and placed in PBST and 3% skim milk containing goat anti-mouse IgG conjugated to horseradish peroxidase (Kirkgaard & Perry Laboratories, Gaithersburg, Md.) for 2 hours at 25° C. Then ricin specific bands were detected by placing the membranes in TMB Membrane Substrate (Kirkgaard & Perry Laboratories).

EXAMPLE 6

Evaluation of Mabs as Immunodiagnostic Reagents

The Mabs were evaluated for their ability to detect antigen directly bound to a solid-phase surface. Microtiter plates were coated with 4 ng/well of antigen. After washing to remove unbound antigen, antibody was serially diluted two-fold in the wells with antigen. Alkaline phosphatase labeled rabbit anti-mouse IgG was used to detect the presence of Mab. The absorbance at 405 nm for each well was determined and used to quantify the amount of antibody bound to antigen. Endpoint titer was determined to be the reciprocal of the highest dilution with an $A_{405}>0.2$.

To evaluate the ability of the Mabs to be used as capture reagents, they were diluted serially two-fold and allowed to bind to the wells of the microtiter plate. After washing to remove unbound Mab, 800 pg/well of antigen was allowed to be captured by the antibody. Alkaline phosphatase labeled rabbit anti-mouse IgG was used to detect the presence of bound antigen, and the absorbance at 405 nm was determined for each well. Endpoint titer was determined to be the reciprocal of the highest dilution of Mab that resulted in an $A_{405}>0.2$. For all assays, affinity-purified polyclonal goat anti-RT was used as a control.

EXAMPLE 7

Neutralization of ricin by Mabs using an in vitro Cell Cytoxicity Assay

EL-4 cells (ATCC-TIB39) were maintained in RPMI-1640 medium (Invitrogen) supplemented with 5% fetal calf serum. Mabs (50 μl/well) were serially diluted (1:1) in 96-well flat-bottom tissue culture plates after which 50 μl of RT (40 μl/ml) was added to each well containing serum dilutions. Dilutions of mouse anti-ricin serum and mouse normal serum were included as positive and negative controls. In addition, dilutions of RT were also included for generation of a standard curve for ricin cytotoxicity. The plates were then incubated for 1 hour at 37° C. during which time EL-4 cells were pelleted (600×g, 10 minutes, 4° C.) and resuspended to $5 \times 10^5$ cells/ml in RPMI-1640 media (Invitrogen). The cells were added (100 μl/well) to plates containing RT and dilutions and incubated (37° C., 5% $CO_2$). After 18 hours, 25 μl/well Alamar Blue (Biosource International, Camarillo, Calif.) was added to each well and the plates were incubated for an additional 4 hours (37° C., 5% $CO_2$). The plate reader was first blanked against dye in media only and then absorbance measured at two wavelengths (570 nm and 600 nm) on a Victor plate reader (EG&G Wallac, Turku, Finland). Reduction was then calculated as the difference between absorbance of test wells at 570 nm versus that at 600 nm. Results were calculated as percent inhibition of cytotoxicity relative to the control (Mab+RT+cells/normal serum+RT+cells×100).

EXAMPLE 8

Human Lung Cell Cytotoxicity Assay

Normal human small airway epithelial cells ($1^{st}$ passage) were obtained from Clonetics, Md., USA. Basal serum free growth medium and growth factors were also obtained from Clonetics. Bovine fetal calf serum was obtained from Gibco, Md., USA. Trypsin (porcine—tissue culture tested), ricin ($RCA_{60}$), neutral red (NR) in phosphate-buffered saline (PBS—cell culture tested), thiazolyl blue (MTT), MTT formazan and dimethyl sulfoxide (DMSO—ACS reagent) were all obtained from Sigma. EDTA was a Univar analytical reagent. Glycerol was BDH Analar reagent obtained from Merck. Affinity purified goat polyclonal anti-ricin antibody was a generous gift from Dr. Mark Poli, USAMRIID, USA. Tissue-culture-treated 96-well microplates were obtained from Costar® (product # 3596).

A. Cell Culture of Small Airway Epithelial (SAE) Cells

Cells were cultured in a serum free complete medium (SAGM) prepared from the basal medium and growth factors supplied by Clonetics. For the preparation of $2^{nd}$ or $3^{rd}$ passage cells, thawing of the $1^{st}$ passage cryo-preserved cells was rapidly initiated by transient immersion of the vial in water at 40° C. The resultant concentrated suspension of cells was gently diluted into 20 ml of SAGM, mixed and centrifuged at 240 g to pellet the cells. The cells in the pellet were re-suspended in sufficient SAGM to allow a seeding density of $2.5 \times 10^3$ cells/$cm^2$ in 75 $cm^2$ vented culture flasks. Incubation in an atmosphere of 5% $CO_2$ in air was at 37° C. The medium was exchanged for fresh SAGM on the $2^{nd}$ day after seeding and thereafter every 2 or 3 days. The cells were harvested when about 80% confluent by exchanging the culture medium for a freshly prepared mixture of trypsin (0.05%), EDTA (0.01%) and glucose (0.05%) in PBS at 37° C. When cells were detached, trypsin activity was stopped by adding 10% fetal calf serum (FCS) in SAGM, also at 37° C., in a 1:1 ratio to the trypsin-containing medium. The cell suspension was centrifuged and the pelleted cells re-suspended in the above stopping solution (10% FCS in SAGM) for counting using a Neubauer Haemocytometer.

For storage, the cells were re-suspended at 37° C. and an equal volume of sterile 20% glycerol in stopping solution (also at 37° C.) added very slowly with gentle shaking. 1 ml of the resultant cell suspension was dispensed per cryovial ($8 \times 10^5$ cells/vial) for freezing. The cryovials were then placed in an isopropanol-charged plastic cryo-chamber and cooled to and maintained at −80° C. for at least about 24 hours. Long-term storage was under liquid nitrogen.

For the seeding of cells in 96-well microplates, a vial of $3^{rd}$ passage cells was thawed and washed as above. The cells were then re-suspended in the appropriate volume of SAGM to allow 200 μl aliquots each containing $(1–4) \times 10^4$ cells to be dispensed per well as required.

B. Optimization of OD Measurements

To study the effect of seeding density on OD development due to NR uptake or MTT-formazan formation, cells were two-fold serially diluted in the microplate within the range of (2 or 4)×$10^4$ to (1.25 or 2.5)×$10^3$ cells/well, respectively. See Borenfreund, E. and Puerner, J. A. (1985) Absorption. Toxicol. Lett. 24(2–3):119–124; Loik, C. W., et al. (1993) Anal. Biochem. 213(2):426–433; and Figenschau, Y., et al. (1997) J. Environ. Sci. Health. B. 32(2):177–194, which are herein incorporated by reference. Incubation periods at 37° C. and in the presence of 5% $CO_2$ included 1–2 days for cell adhesion and recovery plus up to 4 days for proliferation. During this time the growth medium was replaced once—on the $3^{rd}$ day.

C. Preparation of Medium for NR and MTT Assays

NR was prepared at 50 μg/ml using methods known in the art. See Kull, F. C. Jr., and Cuatrecasas, P. (1983) Appl. Biochem. Biotechnol. 8(2):97–103; and Borenfreund, E. and Puerner J. A. (1985) Absorption. Toxicol. Lett. 24(2–3): 119–124, which are herein incorporated by reference. Toxicity was determined in vitro by morphological alterations and neutral red absorption by dilution of the sterile stock solution with SAGM. MTT stock solution was prepared at 5 mg/ml in PBS and sterilized by passage through a 0.22 μm filter (Millex® GV.4) before being diluted to 0.5 mg/ml in SAGM. See Mosmann, T. (1983) J. Immunol. Methods 65(1–2):55–63; and Plumb, J. A., et al. (1989) Cancer Res. 49(16):4435–4440; Figenschau, Y., et al. (1997) J. Environ. Sci. Health B. 32(2):177–194, which are herein incorporated by reference. Before use, both solutions were incubated at 37° C. for 15 minutes and centrifuged at 1500 g to pellet out any precipitate/crystals formed.

D. Measurement of Cell Viability Using NR Uptake

Uptake of NR into viable cells was measured after incubation in the NR-containing growth medium (200 μl/well) for 3 hours at 37° C. and in the presence of 5% $CO_2$. See Borenfreund, E. and Puerner J. A. (1985) Absorption. Toxicol. Lett. 24(2–3):119–124, which is herein incorporated by reference. In the initial experiments the cells were washed once with SAGM (200 μl/well) without any fixation, and the NR extracted for 1 hour with 1% v/v acetic acid in 50% ethanol. In later experiments, after the initial wash with SAGM, the dye was extracted with 0.3% v/v conc. HCl in DMSO (200 μl/well) for 1 hour. In both cases, the absorbance was measured at 540 nm (TiterTek MS212).

E. Measurement of Viability Using MTT-Formazan Formation

The conversion of MTT to its blue formazan by viable cells was measured after incubation in MTT-containing SAGM (200 μl/well) for 3 hours at 37° C. and in the presence of 5% $CO_2$. See Denizot, F. and Lang, R. (1986) J. Immunol. Methods 89(2):271–277; Twentyman, P. R. and Luscombe, M. (1987) Br. J. Cancer 56(3):279–285; Figenschau, Y., and Yousef, M. I. (1997) J. Environ. Sci. Health B. 32(2):177–194, which are herein incorporated by reference. The cells were then washed with SAGM (200 μl/well) before dye extraction. In the initial experiments the cells were extracted with 0.3% v/v HCl in isopropanol but later, because of high blanks, 0.3% HCl in DMSO or DMSO (200 μl/well) was used. See Mosmann, T. (1983) J. Immunol. Methods 65(1–2):55-63; Figenschau, Y., and Yousef, M.I. (1997) J. Environ. Sci. Health B. 32(2):177–194; Twentyman, P. R. and Luscombe, M. (1987) Br. J. Cancer 56(3): 279–285; and Plumb, J. A., et al. (1989) Cancer Res. 49(16):4435–4440, which are herein incorporated by reference. After extraction the OD at 540 nm was measured.

F. Exposure of SAE cells to ricin

Aliquots of ricin stock solution were diluted initially into PBS and then into SAGM to give the appropriate concentration. The resultant solutions were sterilized by passage through a 0.22μ Millex® filter. In ricin concentration-effect studies serial two-fold dilutions of 250 pM ricin medium to 0.5 pM (or of 100 pM ricin medium to 0.8 pM) were carried out in separate 96-well microplates. Cells were exposed to 200 μl of the diluted ricin media for 24 or 72 hours on the $4^{th}$ day after seeding, or for 24 hours on the $6^{th}$ day after seeding. Measurements of NR uptake or MTT-formazan formation were on day 7.

G. Exposure of SAE cells to ricin and polyclonal antibody

The antibody stock solution (2 mg/ml in PBS) was partially diluted in PBS and then into SAGM to an estimated concentration of 260 pM. To study the effect of a fixed concentration of ricin (7 pM) in the presence of variable amounts of antibody on cell growth, further serial two-fold dilutions of this antibody medium from 260 pM to 8 pM were first carried out in separate 96-well microplates. These concentrations were subsequently halved by the addition of an equal volume of ricin in SAGM. Cells were exposed to these antibody-ricin mixtures for 24 hours on the $6^{th}$ day after seeding. Measurements of NR uptake or MTT-formazan formation were on day 7.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

I claim:

1. A monoclonal antibody produced by a hybridoma deposited in the American Type Culture Collection selected from the group consisting of ATCC accession numbers PTA-6105, PTA-6106, PTA-6107, PTA-6108, PTA-6109, and PTA-6110.

2. A hybridoma deposited in the American Type Culture Collection selected from the group consisting of ATCC accession numbers PTA-6105, PTA-6106, PTA-6107, PTA-6108, PTA-6109, and PTA-6110.

3. A composition comprising at least one monoclonal antibody of claim 1 in a pharmaceutically acceptable carrier.

4. The composition of claim 3, and further comprising a supplementary active compound.

5. A method for assaying, detecting, measuring, or monitoring ricin toxin, ricin toxin A-chain, ricin toxin B-chain, or a combination thereof in a sample which comprises contacting at least one monoclonal antibody according to claim 1 with the sample evaluating any complex between the monoclonal antibody with ricin toxin ricin toxin A-chain, or ricin toxin B-chain.

6. A method for obtaining ricin toxin, ricin toxin A-chain, ricin toxin B-chain, or a combination thereof from a sample which comprises using at least one monoclonal antibody according to claim 1 as a capture reagent.

7. A kit comprising at least one monoclonal antibody of claim 1 packaged together with instructions for use.

* * * * *